(12) United States Patent
Choi et al.

(10) Patent No.: US 10,139,591 B2
(45) Date of Patent: Nov. 27, 2018

(54) ASPHERICAL MIRROR FOR FOCUSING LASER BEAM IN LINEAR PATTERN AND LASER SURGERY DEVICE EQUIPPED WITH SAME

(71) Applicant: Korea University Research and Business Foundation, Seoul (KR)

(72) Inventors: Won-shik Choi, Seoul (KR); Jung-ho Moon, Busan (KR); Seung-Kuk Baek, Seoul (KR); Jung Joo Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/632,827

(22) Filed: Jun. 26, 2017

(65) Prior Publication Data
US 2018/0011288 A1     Jan. 11, 2018

(30) Foreign Application Priority Data

Jul. 7, 2016     (KR) .................. 10-2016-0086062

(51) Int. Cl.
*G02B 13/00*     (2006.01)
*G02B 5/10*     (2006.01)
(Continued)

(52) U.S. Cl.
CPC .......... *G02B 13/002* (2013.01); *A61F 9/0084* (2013.01); *G02B 5/10* (2013.01);
(Continued)

(58) Field of Classification Search
CPC .. G02B 13/002; G02B 13/007; G02B 5/0808; G02B 13/0055; G02B 13/0065; G02B 13/0075; G02B 27/09; G02B 5/10; A61F 9/0084; A61F 9/007; A61F 9/008; A61F 9/00821
(Continued)

(56) References Cited

U.S. PATENT DOCUMENTS 3,957,031 A * 5/1976 Winston .................... F21V 7/00
                                                  126/695
4,116,540 A * 9/1978 Thomas .................... G02B 5/10
                                                  359/869
(Continued)

FOREIGN PATENT DOCUMENTS

KR    10-2008-0086642 A    9/2008
KR    10-2010-0032676 A    3/2010
(Continued)

*Primary Examiner* — Jordan Schwartz
(74) *Attorney, Agent, or Firm* — NSIP Law (57) ABSTRACT

According to an embodiment of the present invention, there is provided an aspherical mirror for focusing a laser beam in a linear pattern, the aspherical mirror including: a convex surface diffusely reflecting an irradiated laser beam; and a concave surface reflecting the laser beam such that the laser beam is focused at one point, wherein the laser beam reflected from the convex surface forms a long line beam as an angle of reflection with respect to a curvature of the convex surface changes, and the laser beam reflected from the concave surface is focused at one point on the line beam as an angle of reflection with respect to a curvature of the concave surface changes.

6 Claims, 9 Drawing Sheets

(51) Int. Cl.
*G02B 5/08* (2006.01)
*A61F 9/008* (2006.01)
*G02B 27/09* (2006.01)

(52) U.S. Cl.
CPC ...... *G02B 13/0065* (2013.01); *A61F 9/00821* (2013.01); *G02B 27/09* (2013.01)

(58) Field of Classification Search
USPC .................................................. 359/867–869
See application file for complete search history.

(56) References Cited

U.S. PATENT DOCUMENTS

| | | | |
|---|---|---|---|
| 5,592,582 A * | 1/1997 | Oparin | B23K 28/00 250/504 R |
| 8,262,647 B2 | 9/2012 | Raksi et al. | |
| 2013/0033774 A1* | 2/2013 | Hashimoto | B60R 1/082 359/850 |
| 2015/0051591 A1 | 2/2015 | Hanebuchi et al. | |
| 2016/0170190 A1* | 6/2016 | Hou | G02B 17/0636 359/859 |

FOREIGN PATENT DOCUMENTS

| | | |
|---|---|---|
| KR | 10-2013-0129351 A | 11/2013 |
| KR | 10-2015-0050357 A | 5/2015 |
| KR | 10-1574951 B1 | 12/2015 |

\* cited by examiner

ASPHERICAL MIRROR FOR FOCUSING LASER BEAM IN LINEAR PATTERN AND LASER SURGERY DEVICE EQUIPPED WITH SAME

CROSS REFERENCE TO RELATED APPLICATION

The present application claims priority to Korean Patent Application No. 10-2016-0086062, filed Jul. 7, 2016, the entire contents of which is incorporated herein for all purposes by this reference.

BACKGROUND OF THE INVENTION

Field of the Invention

The present invention relates generally to an aspherical mirror for focusing a laser beam in a linear pattern and a laser surgery device equipped with the aspherical mirror. More particularly, the present invention relates to an aspherical mirror for focusing a laser beam in a linear pattern and a laser surgery device equipped with the aspherical mirror, in which a convex surface and concave surface, onto which a laser beam is reflected, are configured to have a predetermined curvature, thereby focusing a laser beam in a linear pattern.

Description of the Related Art

A conventional tissue resection device is configured such that living tissue is resected by heating the tissue by applying a current thereto. However, this conventional method is problematic in that excessive heat may be transmitted to the cut portion or damage to surrounding tissue may occur. Accordingly, techniques for tissue resection devices using ultrasound and a laser beam are being developed.

A tissue resection technique using ultrasound is performed in such a way that a high frequency of tens of thousands of Hz is applied to a piezoelectric crystal, and the ultrasound from the crystal moves the blade of the tip of the device, whereby the blade cuts living tissue. The tissue resection technique using ultrasound minimizes damage to surrounding tissue since the blade works with ultrasound. Further, the tissue resection technique using ultrasound is capable of immediately stopping bleeding of surrounding tissue by using heat generated by the ultrasound.

The tissue resection technique using ultrasound is advantageous in that since the resection time is short and the closing of the blood vessels and resection operation are performed at the same time, it is easy to use. However, the tissue resection technique using ultrasound is problematic in that since the vibration of the device is forced to move back and forth, it is impossible to make a joint structure in the device.

Meanwhile, a tissue resection technique using a laser beam is performed in such a way that when a laser beam is absorbed into living tissue, the temperature of the tissue is raised, and when the temperature reaches 100° C., the water inside the tissue is boiled and expands rapidly, whereby the tissue bursts and is ablated by water vapor bubbles.

The tissue resection technique using a laser beam is capable of focusing a laser beam to a very small size of 0.1 mm and is capable of heating a living tissue faster than the heat diffusion rate in tissue through pulse modulation. Thereby, the tissue resection technique using a laser beam is capable of minimizing damage to surrounding tissue. Further, the tissue resection technique using a laser beam is capable of immediately stopping bleeding by irradiating a laser beam onto the surrounding tissue after resection.

However, the conventional tissue resection technique using a laser beam is designed in such a way that a laser beam is focused in a straight line by using a spherical lens and a cylindrical lens, and the focused laser beam is transmitted to a living tissue using a flat mirror. In this case, an installation space that corresponds to the sizes of the spherical lens, the cylindrical lens, and the mirror, and a space that corresponds to both a focal length of the spherical lens and a focal length of the cylindrical lens are required. Due to this, it is difficult to shorten the entire length of the tissue resection device to a few cm or less.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Japanese Patent Application Publication No. 2014061214A (a laser handpiece is disclosed)

SUMMARY OF THE INVENTION

Accordingly, the present invention has been made keeping in mind the above problems occurring in the related art, and the present invention is intended to propose an aspherical mirror for focusing a laser beam in a linear pattern, in which a convex surface and concave surface, onto which a laser beam is reflected, are configured to have a predetermined curvature, thereby focusing and reflecting an incident laser beam in a linear pattern.

The present invention is further intended to propose a laser surgery device equipped with an aspherical mirror, which is capable of focusing and reflecting a laser beam in a linear pattern by using one aspherical mirror, without using a spherical lens and a cylindrical lens that are required in the conventional optical system, whereby it is possible to minimize the size of the device by eliminating an installation space of the lens with the focal length between multiple lenses reflected.

The present invention is further intended to propose a laser surgery device equipped with an aspherical mirror, which is configured such that a laser beam provided from an optical fiber is converted into a line beam by only using one aspherical mirror, whereby it is possible to minimize a size of an optical system.

In order to achieve the above object, according to one aspect of the present invention, there is provided an aspherical mirror for focusing a laser beam in a linear pattern, the aspherical mirror including: a convex surface diffusely reflecting an irradiated laser beam; and a concave surface reflecting the laser beam such that the laser beam is focused at one point, wherein the laser beam reflected from the convex surface forms a long line beam as an angle of reflection with respect to a curvature of the convex surface changes, and the laser beam reflected from the concave surface is focused at one point on the line beam as an angle of reflection with respect to a curvature of the concave surface changes.

In an embodiment of the present invention, it is preferred that the aspherical mirror has a saddle-shaped structure with a curved cross section.

In order to achieve the above object, according to another aspect of the present invention, there is provided a laser surgery device equipped with an aspherical mirror, the laser surgery device including: an aspherical mirror for focusing a laser beam in a linear pattern; a tissue gripper being equipped with the aspherical mirror, and having a joint structure configured to grip and release a human body tissue; and a laser beam irradiator irradiating the laser beam onto the aspherical mirror by being connected to the tissue gripper, wherein the laser beam is reflected along a curvature of the aspherical mirror to be in a line beam, and is irradiated onto the human body tissue gripped by the tissue gripper.

In an embodiment of the present invention, it is preferred that the aspherical mirror has a saddle-shaped structure with a curved cross section.

In an embodiment of the present invention, it is preferred that the tissue gripper includes: a first housing accommodating the aspherical mirror therein; and a second housing connected to the first housing to be in a tongs structure, wherein the first housing and the second housing grip the human body tissue through a gripping motion.

In an embodiment of the present invention, it is preferred that the first housing is provided with a transmission opening at a surface that grips the human body tissue, with the line beam passing through the transmission opening, wherein the transmission opening is provided along a longitudinal direction of the first housing.

The aspherical mirror for focusing a laser beam in a linear pattern of the present invention is advantageous in that it is possible to convert a laser beam provided from an optical fiber into a line beam by using a convex surface and a concave surface of the aspherical mirror without using a spherical lens and a cylindrical lens that are required in the conventional optical system.

Thereby, the present invention is capable of minimizing an entire size of an optical system that converts a laser beam into a line beam. In other words, since the present invention is capable of focusing a laser beam in a linear pattern by using one aspherical mirror, when compared to the conventional case where a laser beam is converted into a line beam by using multiple lenses and one mirror, it is possible to minimize the size of the optical system by eliminating an installation space of the lens with the focal length between multiple lenses considered.

The present invention is further advantageous in that since a laser beam is converted into a line beam by only using one aspherical mirror, it is possible to prevent the laser beam from losing energy in the process where the laser beam is focused in the form of a line beam via multiple lenses.

The laser surgery device equipped with the aspherical mirror, as the present invention, is capable of being configured with a joint structure, whereby it may be applied not only to the abdominal cavity but also to the neck by maximizing accessibility to the surgical site and convenience.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, an aspherical mirror for focusing a laser beam in a linear pattern and a laser surgery device equipped with the aspherical mirror according to an exemplary embodiment of the present invention will be described in detail with reference to the accompanying drawings.

Firstly, reference will be made to an aspherical mirror for focusing a laser beam in a linear pattern, hereinbelow.

Figure 1:
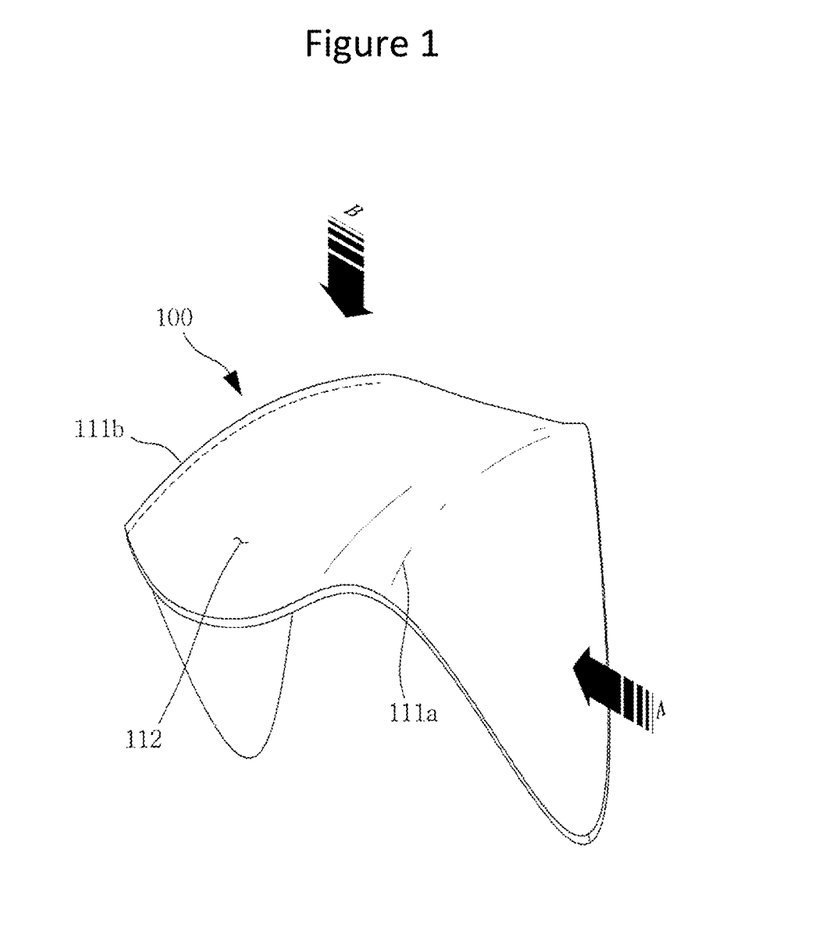
FIG. 1 is a schematic perspective view showing an aspherical mirror for focusing a laser beam in a linear pattern according to an embodiment of the present invention.
Figure 2:
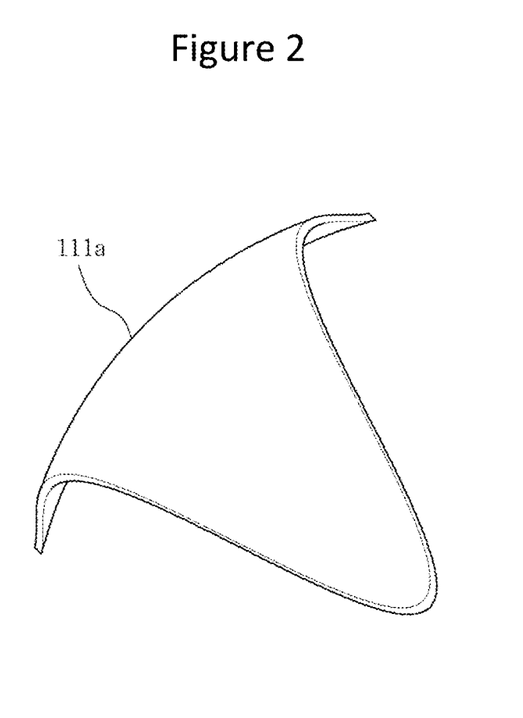
FIG. 2 is a schematic side view showing the aspherical mirror for focusing a laser beam in a linear pattern viewed from direction A of FIG. 1.
Figure 3:
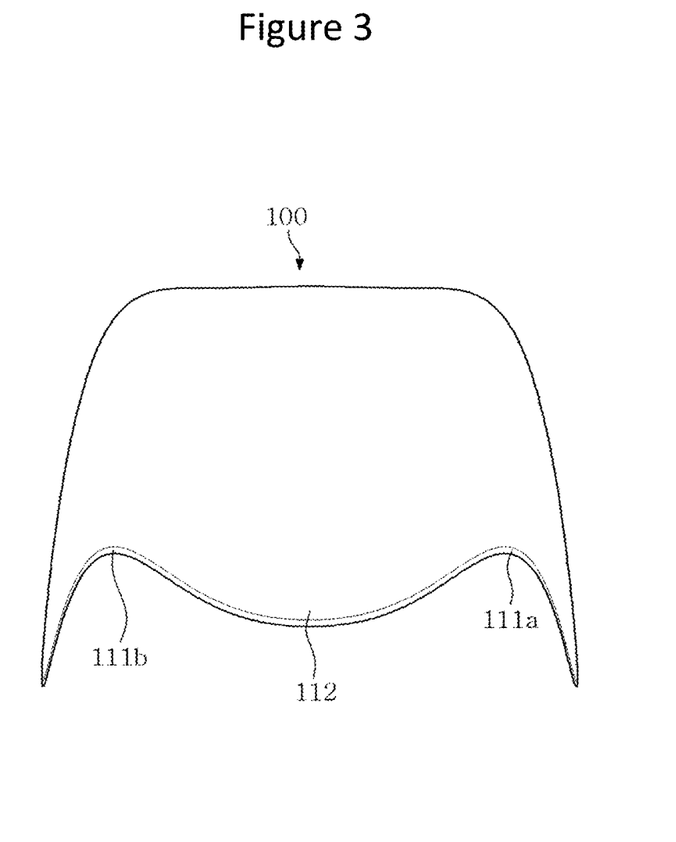
FIG. 3 is a schematic plane view showing the aspherical mirror for focusing a laser beam in a linear pattern viewed from direction B of FIG. 1.
Figure 4:
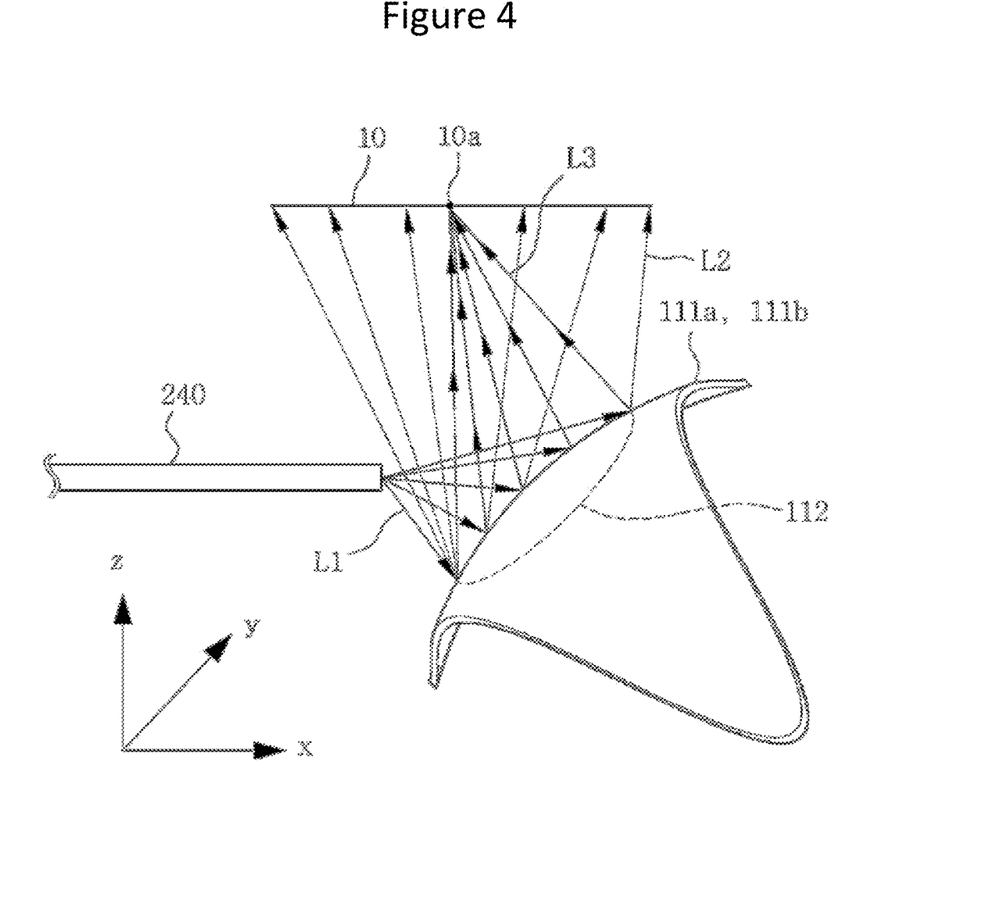
FIG. 4 is a schematic view showing a path of a laser beam irradiated onto the aspherical mirror for focusing a laser beam in a linear pattern.
Figure 5:
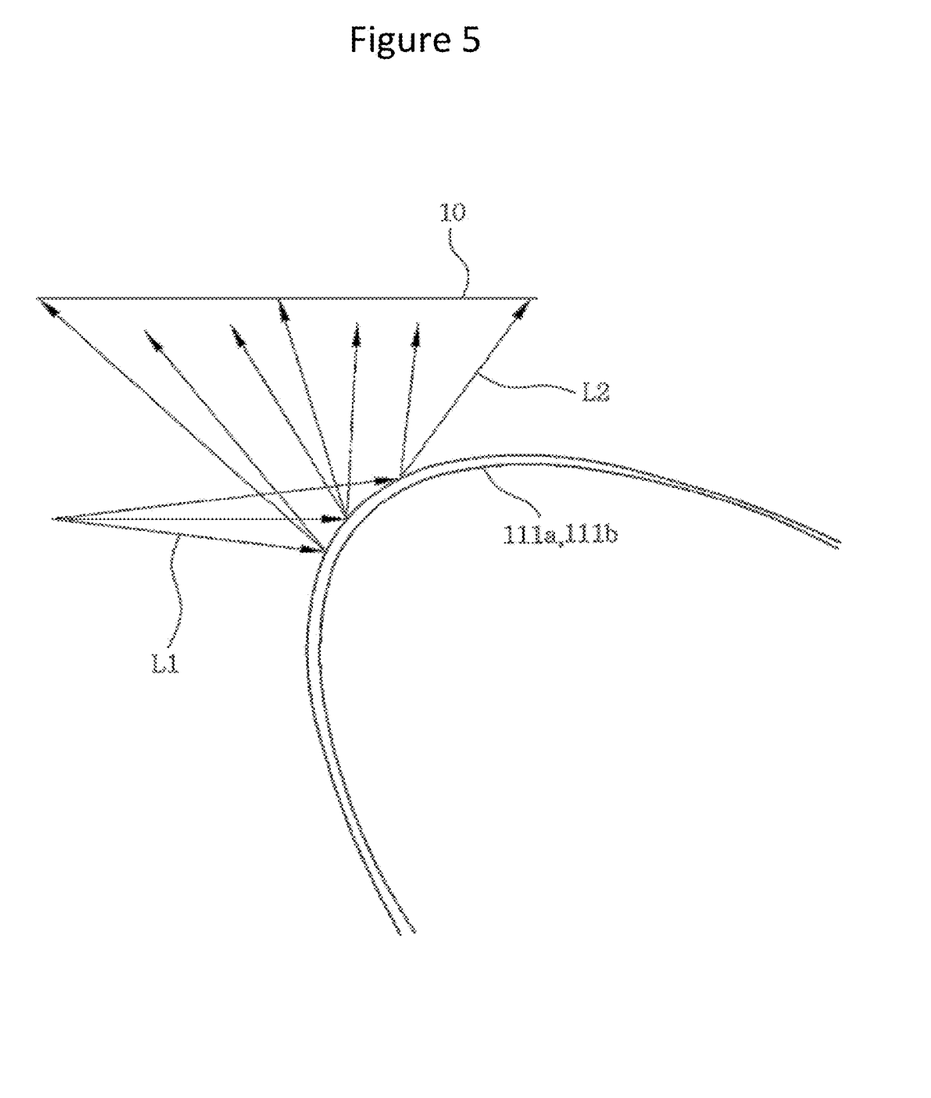
FIG. 5 is a schematic view showing a path of a laser beam reflected from a convex surface of the aspherical mirror for focusing a laser beam in a linear pattern.
Figure 6:
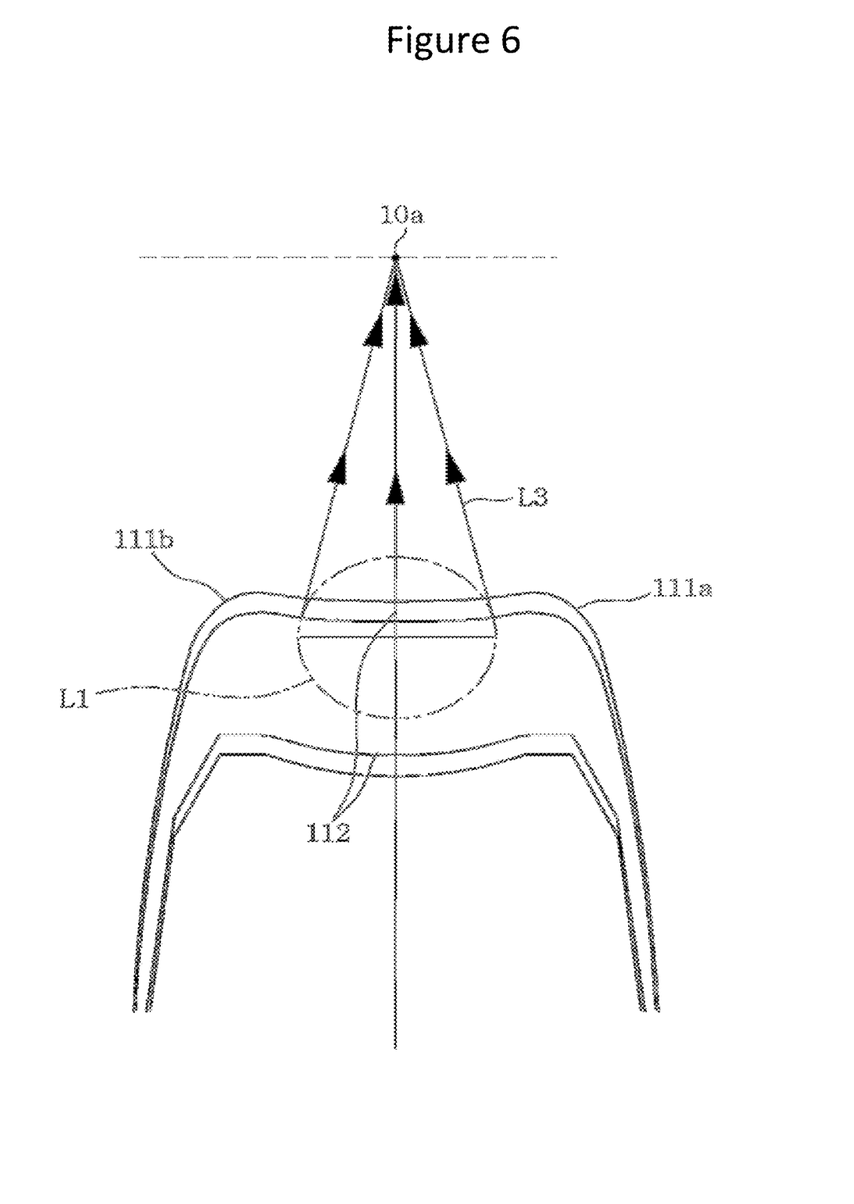
FIG. 6 is a schematic view showing a path of a laser beam reflected from a concave surface of the aspherical mirror for focusing a laser beam in a linear pattern.

FIG. 1 is a perspective view showing an aspherical mirror for focusing a laser beam in a linear pattern according to an embodiment of the present invention; FIG. 2 is a side view showing the aspherical mirror for focusing a laser beam in a linear pattern viewed from direction A of FIG. 1; and FIG. 3 is a plane view showing the aspherical mirror for focusing a laser beam in a linear pattern viewed from direction B of FIG. 1. Further, FIGS. 4 to 6 are schematic views showing a path of a laser beam irradiated onto the aspherical mirror for focusing a laser beam in a linear pattern.

An aspherical mirror 100 for focusing a laser beam in a linear pattern is a mirror that reflects an irradiated laser beam L1. As shown in FIGS. 1 and 3, the aspherical mirror 100 is configured to have a saddle-shaped structure, in which a surface thereof is curved to be both convex and concave with a predetermined curvature. The surface of the aspherical mirror 100 is constituted by convex surfaces 111a and 111b and a concave surface 112.

In the description, other than parts designated by reference numerals, the convex surface refers to all convex parts when looking at the overall shape of the aspherical mirror 100. Of course, other than parts designated by reference numerals, the concave surface 112 refers to all concave parts when looking at the overall shape of the aspherical mirror 100.

As shown in FIG. 1, the convex surfaces 111a and 111b are surfaces that are curved to be convex with a predetermined curvature. As shown in FIG. 4, the convex surfaces 111a and 111b are reflective surfaces formed in a convex mirror, which diffusely reflect the incident laser beam L1. The laser beam L1 is irradiated by a laser beam irradiator 240, which will be described hereinafter.

The convex surfaces 111a and 111b reflect the laser beam L1 such that the laser beam L1 diffuses according to the curvature of the convex surfaces, rather than simply reflecting. A laser beam L2 is irradiated in a long line beam 10 while being diffusely reflected in response to the curvature of the convex surfaces 111a and 111b.

As shown in FIG. 4, the laser beam L1 incident in an x-axis direction is reflected onto the convex surfaces 111a and 111b to go up along a z-axis direction, and diffuses along the x-axis direction to be long in length.

Figure 7:
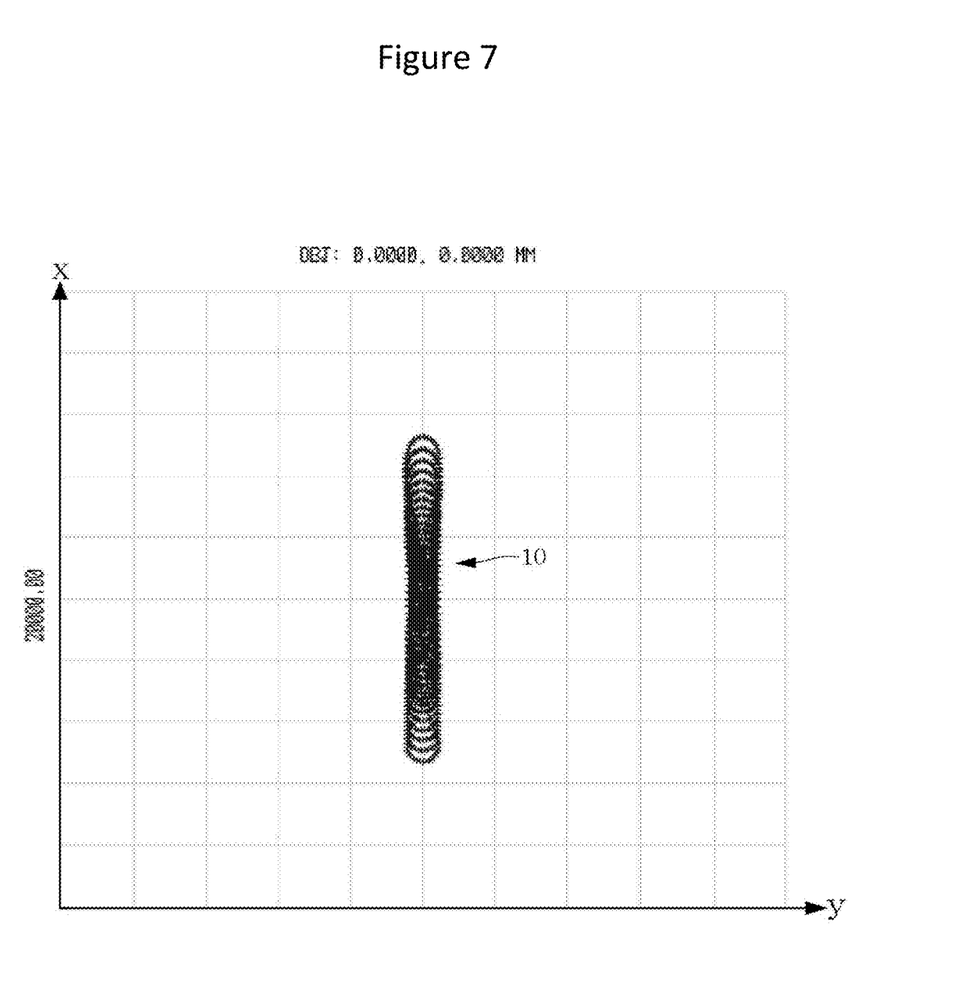
FIG. 7 is a schematic view showing a state where the laser beam reflected from the aspherical mirror for focusing a laser beam in a linear pattern is converted into a line beam along the paths shown in FIGS. 5 and 6.

As shown in FIG. 5, an angle of incidence and an angle of reflection of the laser beam L2 reflected onto the convex surfaces 111a and 111b change in response to the curvature of the convex surfaces 111a and 111b, thereby as shown in FIG. 7, forming the long line beam 10. FIG. 7 is a schematic view showing a state where the laser beam reflected from the aspherical mirror for focusing a laser beam in a linear pattern is converted into a line beam along the paths shown in FIGS. 5 and 6.

As shown in FIGS. 1 and 3, the concave surface 112 is provided between the convex surface 111a and the neighboring convex surface 111b. The concave surface 112 is curved to be concave with a predetermined curvature. The concave surface 112 is in the form of a concave mirror.

As shown in FIGS. 4 and 6, the laser beam L1 irradiated onto the concave surface 112 is reflected as an angle of incidence and an angle of reflection change in response to the curvature of the concave surface 112. As shown in FIG. 6, a laser beam L3 incident on the concave surface 112 is focused at one focus point 10a while being reflected in response to the curvature of the concave surface. It is preferred that the aspherical mirror 100 according to the embodiment is designed such that the focus point 10a is disposed on the line beam 10.

The focus point 10a changes according to changes of the curvature of the concave surface. Since the required focus point 10a may vary according to a size and type of an optical system, in the embodiment, both the curvature of the concave surface 112 and the curvature of the convex surfaces 111a and 111b are not limited to a predetermined curvature.

Reference will be made to a laser surgery device 200 equipped with the aspherical mirror 100, hereinbelow.

Figure 8:
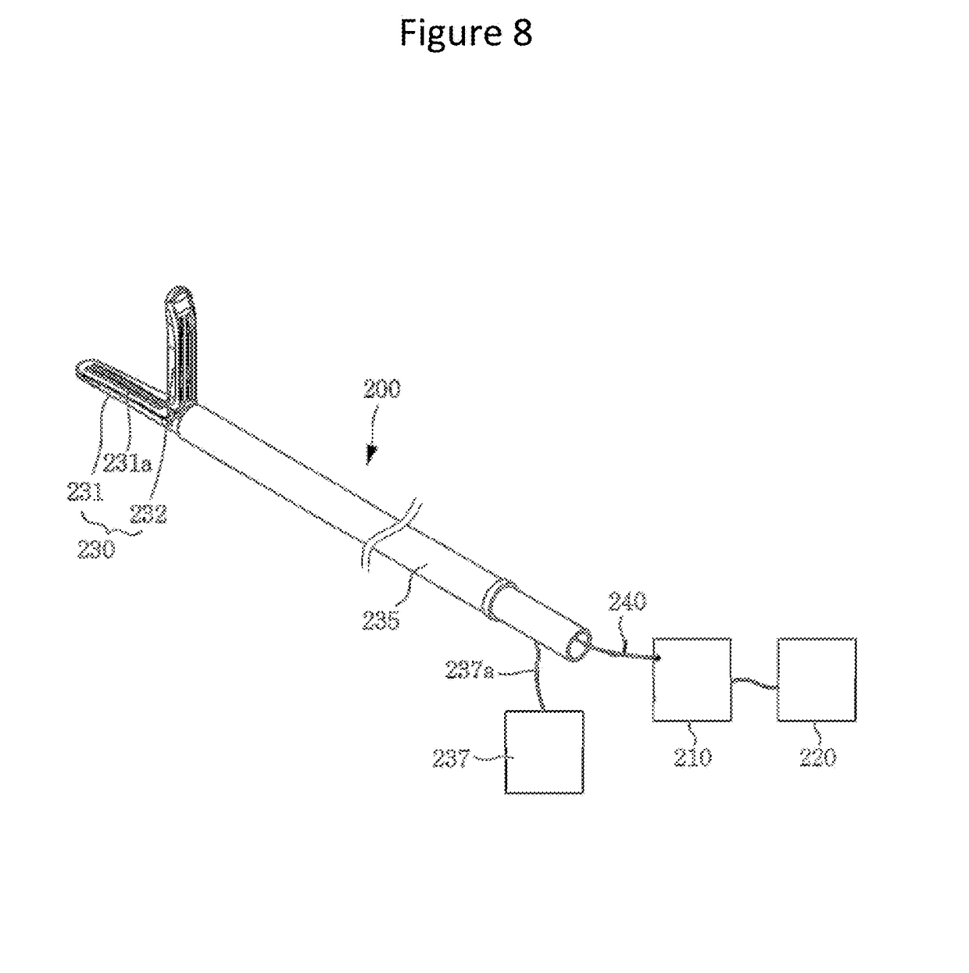
FIG. 8 is a schematic view showing a laser surgery device equipped with the aspherical mirror for focusing a laser beam in a linear pattern according to the embodiment of the present invention.

As shown in FIG. 8, the laser surgery device 200 equipped with an aspherical mirror includes: a tissue gripper 230; the aspherical mirror 100 for focusing a laser beam in a linear pattern; and a laser beam irradiator 240. The laser surgery device 200 is used to resect a human body tissue gripped in the tissue gripper 230 or stop bleeding thereof by using a laser beam L1 as an energy source.

The aspherical mirror 100 is provided inside the tissue gripper 230. The laser beam L1 is reflected to the boundaries between the convex surfaces 111a and 111b, and the concave surface 112 of the aspherical mirror 100, and is irradiated on to the human body tissue gripped in the tissue gripper 230 in the form of the line beam 10.

The laser beam irradiator 240 is provided inside an extension part 235. The laser beam irradiator 240 is connected to a laser beam generator 210. The laser beam generator 210 generates the laser beam L1 when a current is applied thereto. Further, the laser beam generator 210 provides the laser beam L1 to the laser beam irradiator 240. The laser beam generator 210 may be configured such that the intensity of the laser beam L1 is adjusted by a controller 220.

An optical fiber may be used as the laser beam irradiator 240. The laser beam L1 is incident on the aspherical mirror 100 by the laser beam irradiator 240.

The tissue gripper 230 has a structure that can be inserted into the human body. The tissue gripper 230 is in a tongs structure. The tissue gripper 230 is operated to grip and release a human body tissue such as a blood vessel. The tissue gripper 230 is provided with a first housing 231 and a second housing 232. The first housing 231 and the second housing 232 are connected to a manipulation wire 237a of a manipulator 237.

The first housing 231 and the second housing 232 are configured to be folded to grip a human body tissue when the manipulator 237 pulls the manipulation wire 237a. Further, the first housing 231 and the second housing 232 are configured to be unfolded to release the human body tissue when the manipulator 237 releases the manipulation wire 237a.

The aspherical mirror 100 is provided inside the first housing 231. The first housing 231 is provided with a transmission opening 231a. The transmission opening 231a is disposed on a surface where the first housing 231 and the second housing 232 come into contact with each other.

The transmission opening 231a is provided along a longitudinal direction of the first housing 231. The transmission opening 231a is a part, through which the laser beam L1 reflected from the aspherical mirror 100 passes. The transmission opening 231a is sealed by a permeable material (not shown) that allows the laser beam L1 to pass therethrough.

The extension part 235 is connected to the tissue gripper 230. The extension part 235 is in a tubular shape that is flexibly movable. The extension part 235 has a structure that can be inserted into the human body. As shown in FIG. 8, the laser beam irradiator 240 and the manipulation wire 237a are mounted in the extension part 235.

Figure 9:
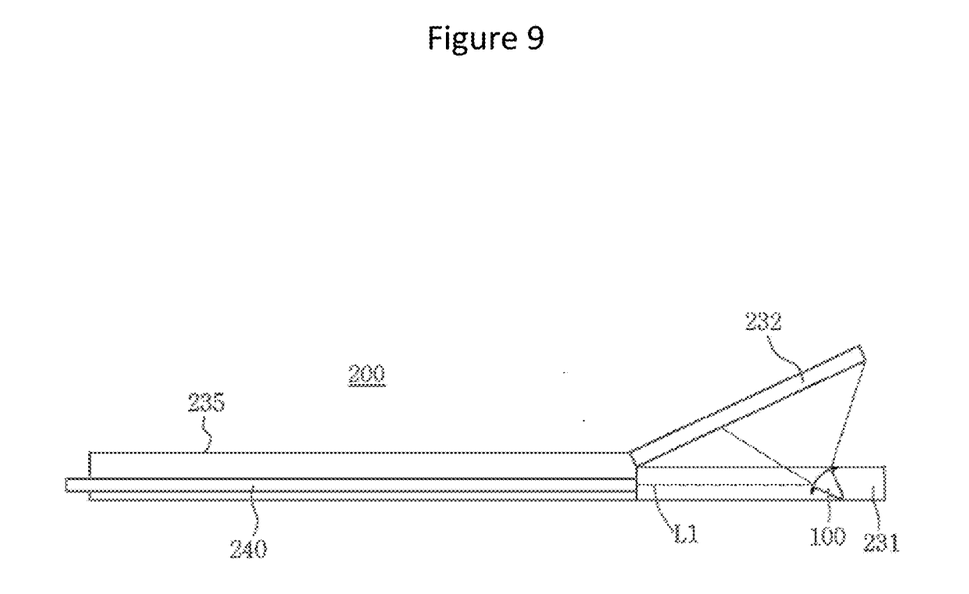
FIG. 9 is a schematic view showing a path of a laser beam when the laser beam is irradiated from an optical fiber in a state where the laser surgery device is provided with the aspherical mirror for focusing a laser beam in a linear pattern therein.

As shown in FIG. 9, the laser beam irradiator 240 transmits the laser beam to the aspherical mirror 100. The laser beam irradiator 240 is disposed in a straight line with the aspherical mirror 100.

The manipulator 237 is connected to the tissue gripper 230 by the manipulation wire 237a. A gripping motion of the tissue gripper 230 is manipulated by the manipulator 237. Manipulation of the gripping motion of the tissue gripper 230 is well known to those skilled in the art, so detailed description on the manipulator 237 will be omitted.

The laser surgery device 200 equipped with the aspherical mirror of the present invention is capable of converting the laser beam L1 into the line beam 10 by simultaneously diffusing and focusing the laser beam L1 using only the aspherical mirror 100.

Thereby, the laser surgery device 200 equipped with the aspherical mirror of the present invention may not require multiple lenses, such as a spherical lens diffusing a laser beam and a cylindrical lens focusing a laser beam, both of which are required in the conventional optical system, so it is possible to reduce a size of the optical system.

Further, the laser surgery device 200 is configured to simultaneously diffuse and focus the laser beam L1 using the aspherical mirror 100, whereby it is possible to reduce energy loss occurring in the process where the laser beam L1 passes through the multiple lenses in the conventional optical system, and it is possible to improve resection efficiency of human body tissue.

The present invention is configured such that the extension part 235 is formed to be a flexibly movable structure to improve accessibility of the tissue gripper 230 to the surgical site, thereby improving an operation success rate by allowing accurate resection at a desired point. Accordingly, the present invention is capable of reducing surgeon fatigue, thereby improving his/her concentration, and is capable of increasing the recovery rate of patient after operation by shortening operation time.

The present invention may be applied not only to the abdominal cavity but also to the neck by maximizing accessibility to the surgical site and convenience through the tongs structure of the tissue gripper 230 and the flexible structure of the extension part 235.

When vascular resection and/or vascular hemeostasis is performed using the present invention configured as described above, a surgeon can fine-tune the intensity of the laser beam L1 according to the type of human body tissue through the controller 220 according to whether hemeostasis or resection is desired, and thus can finely resect or hemostatize the human body tissue. Thereby, it is possible to prevent damage to the surrounding tissue by the laser beam L1, for example, accidental resection of a tissue by irradiating excessive laser beam L1.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An aspherical mirror for focusing a laser beam in a linear pattern, the aspherical mirror comprising:
   a convex surface structured to diffusely reflect an irradiated laser beam; and
   a concave surface structured to reflect the laser beam such that the laser beam is focused at one point, wherein
   the convex surface is so structured such that the laser beam reflected from the convex surface forms a long line beam as an angle of reflection with respect to a curvature of the convex surface changes, and
   the concave surface is so structured such that the laser beam reflected from the concave surface is focused at one point on the line beam as an angle of reflection with respect to a curvature of the concave surface changes.

2. The aspherical mirror of claim 1, wherein
   the aspherical mirror has a saddle-shaped structure with a curved cross section.

3. A laser surgery device equipped with an aspherical mirror, the laser surgery device comprising: a tissue gripper having a joint structure configured to grip and release a human body tissue; the aspherical mirror of claim 1 connected to the tissue gripper; and a laser beam irradiator configured to irradiate the laser beam onto the aspherical mirror, wherein the aspherical mirror is configured to reflect the laser beam such that the laser beam is reflected along a curvature of the aspherical mirror to be in a line beam, and is irradiated onto the human body tissue gripped by the tissue gripper.

4. The laser surgery device of claim 3, wherein
   the aspherical mirror has a saddle-shaped structure with a curved cross section.

5. The laser surgery device of claim 3, wherein the tissue gripper includes:
   a first housing accommodating the aspherical mirror therein; and
   a second housing connected to the first housing to be in a tongs structure, wherein
   the first housing and the second housing are configured to grip the human body tissue through a gripping motion.

6. The laser surgery device of claim 5, wherein
   the first housing is provided with a transmission opening at a surface that grips the human body tissue, wherein
   the transmission opening is provided along a longitudinal direction of the first housing and is configured such that the line beam passes through the transmission opening.

* * * * *